United States Patent [19]

Nakamura et al.

[11] Patent Number: 4,795,250
[45] Date of Patent: Jan. 3, 1989

[54] OPHTHALMIC APPARATUS

[75] Inventors: Yukitsugu Nakamura, Sagamihara; Kohichi Yano, Kawasaki, both of Japan

[73] Assignee: Canon Kabushiki Kaisha, Tokyo, Japan

[21] Appl. No.: 47,474

[22] Filed: May 11, 1987

[30] Foreign Application Priority Data

May 17, 1986 [JP] Japan .................................. 61-112989

[51] Int. Cl.$^4$ ............................................. A61B 3/10
[52] U.S. Cl. .................................... 351/212; 351/213
[58] Field of Search ............... 351/205, 206, 212, 221, 351/213, 245, 247

[56] References Cited

U.S. PATENT DOCUMENTS 4,019,813 4/1977 Cornsweet et al. .................. 351/212
4,043,646 8/1977 Heine et al. .......................... 351/213

Primary Examiner—Rodney B. Bovernick
Assistant Examiner—P. M. Dzierzynski
Attorney, Agent, or Firm—Fitzpatrick, Cella, Harper & Scinto

[57] ABSTRACT

An opthalmic apparatus in which the corneal reflection image of an illuminating light source for observing the front eye part of an eye to be examined is substantially prevented from mixing with the corneal reflection image of a light source for measurement, when the corneal reflection image is measured, to measure the shape of the cornea of the eye to be examined, whereby the accuracy with which the measurement of the shape of the cornea is measured is enhanced.

10 Claims, 5 Drawing Sheets

OPHTHALMIC APPARATUS

BACKGROUND OF THE INVENTION

1. Field of the Invention

This invention relates to an ophthalmic apparatus in which functions, such as measuring the shape of the cornea of an eye to be examined and determining the accuracy of alignment, are provided to an observation device having an illuminating light source for observing the front eye part of the eye to be examined, such as a microscope for surgical operation.

2. Related Background Art

An apparatus in which a microscope for surgical operation is provided with the cornea measuring function is known as an example of an apparatus in which the measuring function is provided to an observation device. This apparatus is used to accurately control the degree of cornea astigmatism or accurately measure the refractive power of the cornea during cornea suturing performed during, for example, a surgical operation for removing a cataract, thereby providing good eyesight after surgical operation. In such an apparatus, there has heretofore been proposed a technique whereby an index mark for measurement, referred to as so-called Mire image having a predetermined shape, for example, a circular slit-like shape, is projected onto the cornea so that the shape of the corneal reflection image thereof can be detected and measured by an electrical sensor.

In this case, however, the illuminating light for observation by the microscope during a surgical operation is very intense and therefore, even if the aforementioned index mark for measurement is projected onto the cornea, the optical information of the corneal reflection image of the projected index mark is affected by the corneal reflection image of the illuminating light source for observation, and it is very difficult to electrically detect such optical information. That is, the cornea has a convex mirror action of strong reflective power, and when the Mire image M for measurement is to be detected as shown in Figure 1 of the accompanying drawings, it is difficult to obtain a signal of good S/N ratio due to the filament image F of an illuminating lamp for observation by the corneal reflection even if the light source for the Mire image M is made intense. In FIG. 1, $l_1$, $l_2$ and $l_3$ designate the directions of measurement for measuring the positions of the Mire image M in three meridian directions.

SUMMARY OF THE INVENTION

It is the object of the present invention to provide an ophthalmic apparatus in which any undesirable influence imparted to a measuring system utilizing corneal reflection to detect optical information for measurement by the corneal reflection image of an illuminating light source for observation can be suppressed or eliminated.

DESCRIPTION OF THE PREFERRED EMBODIMENTS

Figure 1:
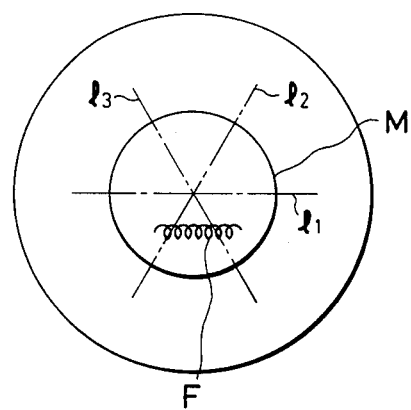
FIG. 1 shows an example of the prior art.
Figure 2A:
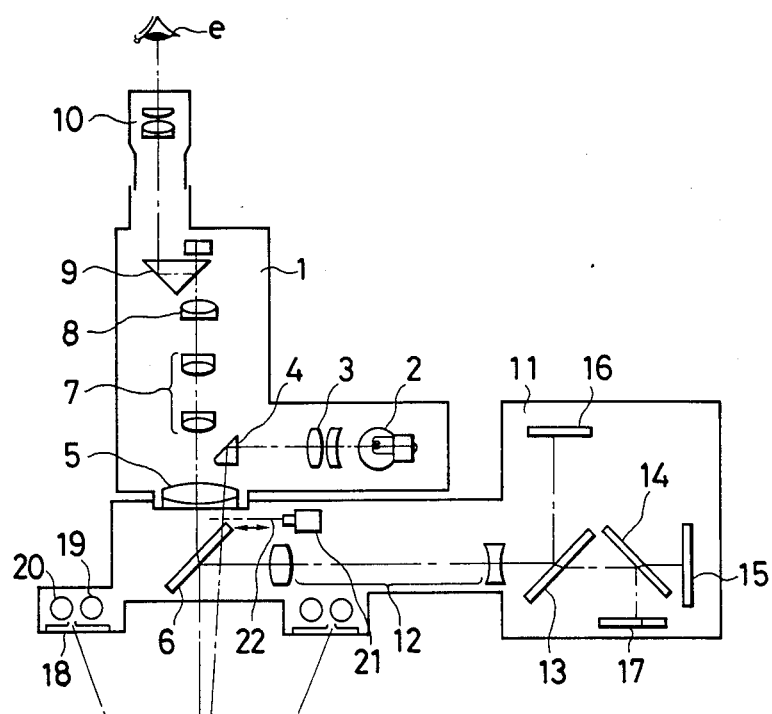
FIGS. 2(A) and (B) show schematic top and plan views, respectively, of the construction of an embodiment of the present invention.
Figure 2B:
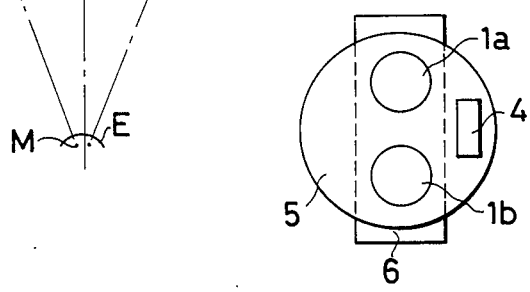

FIGS. 2(A) and (B) show an example of a construction in which a cornea shape measuring device is attached to a microscope for use in a surgical operation. In these figures, reference numeral 1 designates the body of the microscope for use in a surgical operation. The body 1, as shown in the plan view of FIG. 2(B), is provided with microscopes 1a and 1b using in common an objective 5 so that the examiner can stereoscopically observe an eye to be examined. The illuminating light from an illuminating lamp 2 may illuminate the front eye part of the eye E to be examined through a condenser lens 3, a prism lens 4 and the objective 5 so that the examiner e may observe the eye E to be examined by an observation optical system comprising a beam splitter 6, the objective 5, a magnification changing lens 7, an imaging lens 8, an erect prism 9 and an eyepiece 10 arranged in succession in the direction of reflection of the illuminating light. Reference numeral 11 denotes the cornea shape measuring device in which an imaging lens 12, half-mirrors 13 and 14 and a first CCD element 15 are arranged in succession in the direction of reflection of the beam splitter 6, a second CCD element 16 is disposed in the direction of reflection of the half-mirror 13, and a third CCD element 17 is disposed in the direction of reflection of the half-mirror 14. These first, second and third CCD elements 15, 16 and 17 are one-dimensional elements, and their light-receiving surfaces are at positions conjugate with the object side focal plane of the optical system of the microscope for surgical operation, and are disposed in three meridian directions which intersect one another at 60° about a point on the optic axis. A projection index mark 18 for measurement is in the form of a circular slit and may be projected onto the eye E to be examined by the illuminating light of a ring fluorescent lamp 19 for observation or of a ring strobo 20 for measurement so as to form a Mire image M (virtual image) by the corneal reflection on the front eye part of the eye E to be examined. A light-intercepting plate 22 operated by a solenoid 21 is removably disposed in the optical path of the illuminating light.

As is well known, the surface shape of the cornea can be measured by detecting the shape of the Mire image M. The Mire image M is reflected by the beam splitter 6 and passes through the imaging lens 12 of the measuring system, whereafter it is optically divided by the two half-mirrors 13 and 14 and imaged on the light-receiving surfaces of the first, second and third CCD elements 15, 16 and 17. The shape of the Mire image M is detected by the coordinates of points of intersection $a(x_1, y_1)$, $b(x_2, y_2)$, $c(x_3, y_3)$, $d(x_4, y_4)$, $e(x_5, y_5)$, $f(x_6, y_6)$ with the three CCD elements 15, 16 and 17.

By substituting the coordinates of these six points into the general equation of a quadratic curve $$AX^2 + 2HXY + BY^2 + 2GX + 2FY + C = 0$$

and thereby finding each coefficient and effecting operation processing such as coordinates conversion, the longer and shorter diameters of the ellipse and the angle of the axis of the ellipse are found. Subsequently, the radius of curvature of the cornea is calculated from these values, and is further converted to measurement data such as the refractive power of the cornea and the degree of astigmatism of the cornea.

Figure 3:
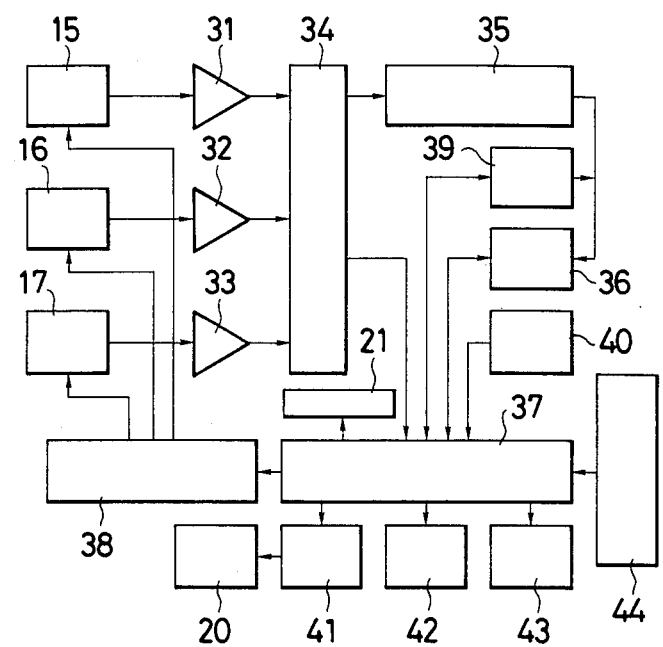
FIGS. 3 and 4 are block circuit construction diagram and a signal wave form diagram, respectively.

A block circuit construction relating to an electric circuit for operation processing is shown in FIG. 3. The outputs of the first, second and third CCD elements 15, 16 and 17 are input to preamplifiers 31, 32 and 33, respectively, and further these signals are input to a multiplexer 34. The output of the multiplexer 34 is connected to an A/D converter 35, RAM 36 and MPU 37 in succession. The output of MPU 37 is designed to control the CCD elements 15, 16 and 17 through a CCD driving circuit 38 and operate RAM 36 by the control of DMAC 39. Reference numeral 40 designates ROM storing a program therein. A signal is output from MPU 37 to a strobo light-emitting circuit 41, an indicator 42 and a printer 43, and the output of the strobo light-emitting circuit 41 is connected to the ring strobo 20. A foot switch 44 for measurement is connected to MPU 37.

When the foot switch 44 is stepped on, a measuring operation is started and the solenoid 21 is first operated by the control of MPU 37, and the light-intercepting plate 22 connected thereto intercepts the illuminating light beam for observation. Subsequently, the three CCD elements 15, 16 and 17 start to accumulate light with the aid of the CCD driving circuit 38 and at the same time, the ring strobo 20 emits light through the ring strobo light-emitting circuit 41. When the accumulation of light is terminated, the output of the multiplexer 34 enters MPU 37 and is controlled by MPU 37, and the solenoid 21 is operated in the return direction, whereby the light-intercepting plate 22 is retracted to a position in which it does not intercept the illuminating light beam for observation, and the eye E to be examined is again illuminated brightly. On the other hand, the output signals of the CCD elements 15, 16 and 17 are amplified by the respective preamplifiers 31, 32 and 33, and then are input to the multiplexer 34. Here, the data of measurement signals supplied as a train of serial signals to the A/D converter 35 and digitalized by the A/D converter 35 are stored in RAM 36 by the control of DMAC 39. The data of RAM 36 are processed by MPU 37 in accordance with the program stored in ROM 40. The measured value can be digital indicated by the indicator 42 and also can be printed out by the printer 43.

Figure 4:
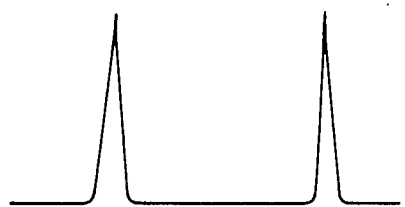

In the above-described embodiment, the switch 44 for measurement is closed when the shape of the cornea is measured, and the intense illuminating light for observation is temporarily intercepted by the light-intercepting plate 22 while the measuring light is detected and therefore, the Mire image M detected by the CCD elements 15, 16 and 17 is converted to an electrical signal of very high S/N ratio and good accuracy as shown in FIG. 4.

In such light-intercepting means for the illuminating light for observation, the light-intercepting plate 22 need not always completely intercept the illuminating light for observation, but may be of such a degree that it partly intercepts the illuminating light beam if the S/N ratio of the detection signal is good. Also, the light-intercepting plate 22 may be a filter or a member having a light-decreasing function which will pass therethrough the light in the form of a grating. As a further alternative, the light-intercepting plate 22 may be a filter which will intercept only a light of a particular wavelength range which will adversely affect the measurement and detection. In these cases, the illuminating light for observation is not completely intercepted and therefore, the examiner can observe the front eye part of the eye to be examined even during measurement. Alternatively, in an apparatus in which the illuminating lamp for observation is not contained in the body of the microscope for surgical operation, but in which a lamp is provided outside the body and illumination is effected through an optical conductor such as glass fiber, the light-intercepting or light-decreasing means as previously described may be provided at the entrance end portion of the optical conductor.

Figure 5:
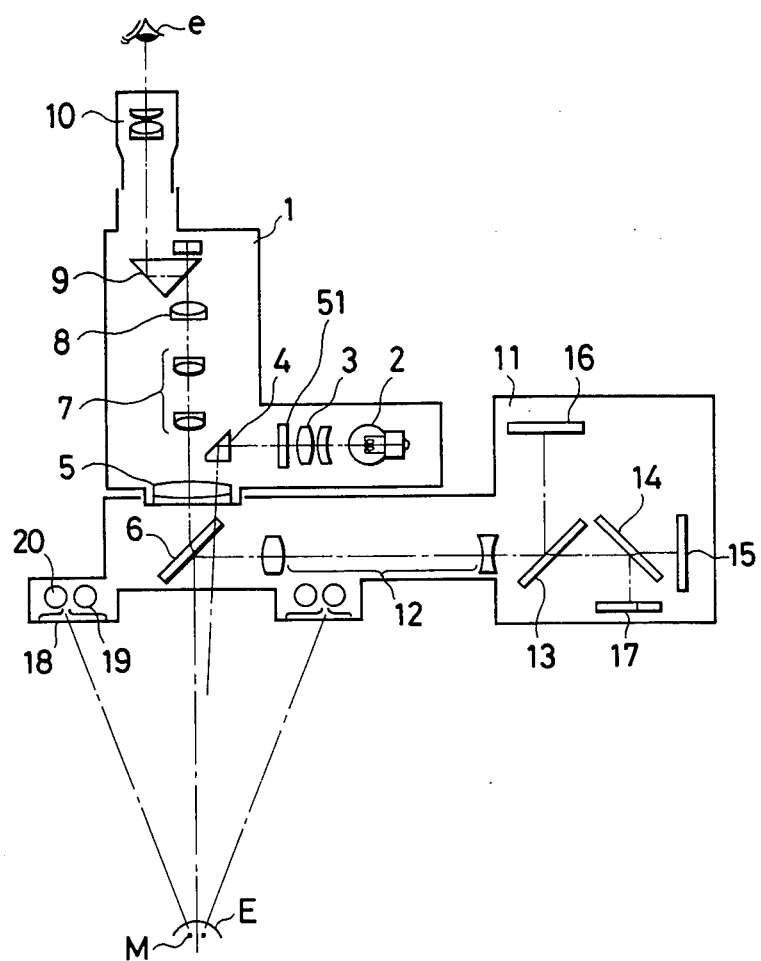
FIGS. 5 and 6 show schematic views of the construction of another embodiment of the present invention.

FIG. 5 shows another embodiment in which, instead of the light-intercepting plate 22 and solenoid 21 of FIG. 2, a transmission type liquid crystal plate 51, which is a member capable of varying the amount of transmitted light, is disposed in the illuminating optical path for observation. In FIG. 5, reference numerals similar to those in FIG. 2 designate similar members. The liquid crystal plate 51 is electrically controlled by the measuring switch 44 of FIG. 3 so that during observation, the liquid crystal plate 51 is in its transparent state and during measurement, the liquid crystal plate 51 is in its opaque state. This method has an advantage that no mechanically operated member is necessary and the degree of freedom of the mounting position is great.

Figure 6:
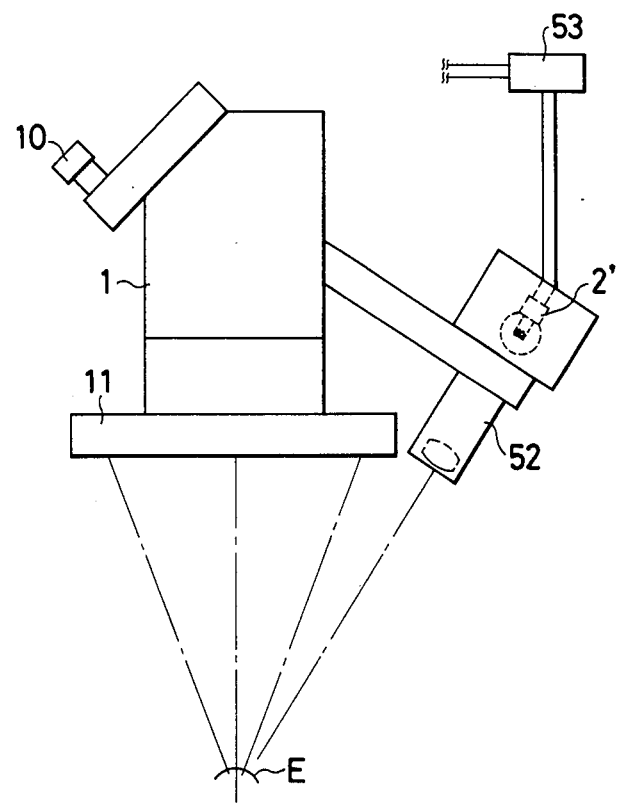

FIG. 6 shows an embodiment in which the illuminating lamp for the observation of the front eye part is adapted to be turned off during measurement. When use is made of the microscope for a surgical operation, the front eye part of the eye E to be examined may be illuminated by an extraneous light source device 52, and in such a case, a relay switch 53 connected to the foot switch 44 is provided instead of operating the solenoid 21 in the block circuit shown in FIG. 3, so that the power source supplied to the illuminating lamp 2' during the measurement of the cornea shape is temporarily cut off or dropped. Of course, it is also possible to design the apparatus such that the illuminating lamp 2 contained in the microscope 1 for a surgical operation as shown in FIG. 2 is once turned off or decreased in illumination by a similar method during measurement.

The foregoing description has been provided of an example in which the cornea shape measuring means is attached to the microscope for a surgical operation; this invention is not so limited it is also conceivable to attach, for example, eye refractive power measuring means or the like to the microscope for a surgical operation and determine the accuracy of alignment by the utilization of the position of the corneal reflection image of the light source for measuring the eye refractive power. That is, as is known from U.S. application Ser. No. 851,861, now U.S. Pat. No. 4,678,297 the corneal reflection image of an index light source for measuring the eye refractive power projected onto the fundus of the eye to be examined can be detected to detect the aligned state thereof with the eye to be examined.

We claim:

1. An ophthalmic apparatus comprising:
   an illuminating observation light source for providing light for observing the front eye part of an eye to be examined:
   an observation system for observing the front eye part of the eye to be examined wherein said observation system is positioned directly in front of the front eye part of the eye;
   a measurement light source, separate from said observation light source, for providing light for effecting predetermined measurement of the eye to be examined;
   a light-receiving optical system for receiving the corneal reflection image of the cornea of the eye illuminated with light produced by said measurement light source;

a light position detector provided on the image surface of said light-receiving optical system for effecting said predetermined measurement of the eye by detecting the position of the corneal reflection image produced by light from said measurement light source; and means for substantially preventing the corneal reflection image of the cornea of the eye produced by light from said illuminating observation light source from being incident upon said light position detector when the position of the corneal reflection image produced by light from said measurement light source is measured by said light position detector.

2. An ophthalmic apparatus according to claim 1, wherein said observation system is a stereoscopic microscope.

3. An ophthalmic apparatus according to claim 1, further comprising a measurement switch for operating said light position detector, and wherein said preventing means is operated in operative association with said measurement switch for operating said light position detector.

4. An ophthalmic apparatus according to claim 3, wherein said preventing means operates in an original state in which the corneal reflection image produced by the light from said observation light source is not prevented from being incident upon said light position detector when said measurement switch prevents said light position detector from measuring the position of the corneal reflection image produced by the light from said measurement light source, wherein said preventing means operates in another state to prevent the corneal reflection image produced by the light from said observation light source from being incident on said light position detector when said measurement switch actuates said light position detector when said measurement switch actuates said light position detector to measure the corneal reflection image produced by the light from said measurement light source, and wherein said preventing means is restored to its original state, in response to the termination of the measurement of the position of the corneal reflection image produced by light from said measurement light source, by said measurement switch.

5. An ophthalmic apparatus according to claim 1, wherein said preventing means intercepts the light for observing produced by said illuminating observation light r source during the measurement of the position of the corneal reflection image produced by light from said measurement light source by said light position detector.

6. An ophthalmic apparatus according to claim 1, wherein said preventing means decreases the light for observing produced by said illuminating observation light source during the measurement of the position of the corneal reflection image produced by light from said measurement light source by said light position detector.

7. An ophthalmic apparatus according to claim 1, wherein said preventing means intercepts only a particular wavelength of the light for observing produced by said illuminating observation light source during the measurement of the position of the corneal reflection image produced by light from said measurement light source by said light position detector.

8. An ophthalmic apparatus according to claim 1, wherein said preventing means comprises a member for changing the degree of transmission of the light for observing produced by said illuminating observation light source, wherein said preventing means further comprises means for inserting said member in the optical path of the light for observing produced by said illuminating observation light source during the measurement of the position of the corneal reflection image produced by light from said measurement light source by said light position detector.

9. An ophthalmic apparatus according to claim 1, wherein said preventing means comprises a liquid crystal for changing the degree of transmission of the light for observing produced by said illuminating observation light source during the measurement of the position of the corneal reflection image produced by light from said measurement light source by said light position detector.

10. An ophthalmic apparatus according to claim 1, wherein said illuminating observation light source produces light in response to the application of electricity thereto, and wherein said preventing means comprises means for changing the amount of electricity supplied to said illuminating observation light source during the measurement of the position of the corneal reflection image produced by light from said measurement light source by said light position detector.

* * * * *